(12) United States Patent
Tsukimura

(10) Patent No.: US 8,040,372 B2
(45) Date of Patent: Oct. 18, 2011

(54) ENCAPSULATED ENDOSCOPE

(75) Inventor: Mitsuhiro Tsukimura, Hachioji (JP)

(73) Assignee: Olympus Corporation, Tokyo (JP)

( * ) Notice: Subject to any disclaimer, the term of this patent is extended or adjusted under 35 U.S.C. 154(b) by 652 days.

(21) Appl. No.: 11/585,080

(22) Filed: Oct. 24, 2006

(65) Prior Publication Data
US 2007/0097294 A1 May 3, 2007

(30) Foreign Application Priority Data
Oct. 28, 2005 (JP) ................................. 2005-313961

(51) Int. Cl.
*A62B 1/04* (2006.01)
*A61B 1/04* (2006.01)

(52) U.S. Cl. ............................. 348/65; 348/45; 348/76

(58) Field of Classification Search ........................ 348/65
See application file for complete search history.

(56) References Cited

U.S. PATENT DOCUMENTS

| | | | | |
|---|---|---|---|---|
| 5,780,884 A | * | 7/1998 | Kumagai et al. | 257/236 |
| 6,507,365 B1 | * | 1/2003 | Nakamura et al. | 348/296 |
| 6,721,005 B1 | * | 4/2004 | Higuchi | 348/243 |
| 7,042,487 B2 | * | 5/2006 | Nakashima | 348/65 |
| 2005/0043583 A1 | * | 2/2005 | Killmann et al. | 600/109 |

FOREIGN PATENT DOCUMENTS

| | | |
|---|---|---|
| DE | 33 37 455 A1 | 4/1984 |
| DE | 103 23 216 B3 | 12/2004 |
| JP | 05227489 A | 9/1993 |
| JP | 2005000552 A | 1/2005 |

OTHER PUBLICATIONS

European Search Report dated Nov. 23, 2007, issued in corresponding European Patent Application No. 06022345.0.

* cited by examiner

*Primary Examiner* — Lin Ye
*Assistant Examiner* — Euel Cowan
(74) *Attorney, Agent, or Firm* — Westerman, Hattori, Daniels & Adrian, LLP

(57) ABSTRACT

An encapsulated endoscope in which exposure amount is controlled at the light source side, and a MOS image sensor is not required to mount a vertical scanning circuit for electronic shutter which is to provide an exposure amount control function. Therefore, since a vertical scanning circuit for electronic shutter is not mounted, the sensor area can be made smaller so that size of the interior of the encapsulated endoscope can be reduced.

1 Claim, 6 Drawing Sheets

US 8,040,372 B2

ENCAPSULATED ENDOSCOPE

This application claims benefit of Japanese Patent Application No. 2005-313961 filed in Japan on Oct. 28, 2005, the contents of which are incorporated by this reference.

BACKGROUND OF THE INVENTION

The present invention relates to an encapsulated endoscope.

It is generally known to provide a vertical scanning circuit for electronic shutter as a means for controlling exposure amount in solid-state imaging apparatus that are used in various imaging apparatus. The construction and method of controlling exposure amount will be described below of a prior-art solid-state imaging apparatus (area sensor) disclosed in Japanese Patent Application Laid-Open Hei-5-227489. FIG. 1 is a block diagram of an overall construction of area sensor 40 as disclosed in the above publication. The area sensor 40 includes: a pixel section 13 having a plurality of pixels two-dimensionally disposed in rows and columns; a vertical scanning circuit 15 (hereinafter referred to as read vertical scanning circuit) for selecting a row of the pixel signals of the pixel section 13 to be read and sequentially switching the selected row; a vertical scanning line 16 for connecting between the pixel section 13 and the read vertical scanning circuit 15; a vertical scanning circuit 42 (hereinafter referred to as electronic shutter vertical scanning circuit) for resetting charge signals accumulated at the pixels; a vertical scanning line 16' for connecting between the pixel section 13 and the electronic shutter vertical scanning circuit 42; a vertical signal line 17 onto which the pixel signals of the rows to be read, selected at the read vertical scanning circuit 15 are outputted; a horizontal read circuit 14 for sequentially outputting the signals outputted onto the vertical signal line 17; and an operation control section 19 for controlling operation of the area sensor 40.

The pixel section 13 consists of a light-receiving pixel region 11 and a light-blocked pixel region 12. The read vertical scanning circuit 15 is provided to the left of the pixel section 13 while the electronic shutter vertical scanning circuit 42 is provided to the right of the pixel section 13.

FIG. 2 is a timing chart for explaining an exposure amount control operation when light is continuously irradiated onto the area sensor 40. Supposing that the scanning direction of the read vertical scanning circuit 15 and the electronic shutter vertical scanning circuit 42 of the area sensor 40 is from the upper portion to the lower portion of the pixel section 13, the signals accumulated at the pixels are reset once between n-th and (n+1)-th frames as shown in the timing chart of the reset signal output and pixel region output of FIG. 2, and pixel signals accumulated again after the resetting are read out. The exposure time (exposure time 1, exposure time 2) for thus read pixel signals is time from the resetting to the readout, i.e., the time difference between the reset timing of a-th row and the read timing of a-th row.

Such exposure time then is proportional to the number of rows occurring between the row (b-th row in the illustrated example) where pixel signals are being reset by the electronic shutter scanning circuit 42 at a point in time t1 when pixel signals (a-th row in the illustrated example) are read out by the read scanning circuit 15 and the row (a-th row) where the pixel signals are being read out by the read scanning circuit 15. The exposure time, therefore, is controlled by changing such number of rows.

In addition, of imaging apparatus for taking images of a dark part for example in the body cavity, there is a method of controlling exposure amount by controlling an emission of light source. FIG. 3 shows an encapsulated endoscope where such exposure amount control method is used as disclosed in Japanese Patent Application Laid-Open 2005-552.

As shown in FIG. 3, an encapsulated endoscope 2 disclosed in the above publication has an outward appearance of a capsule-type tablet form. It includes a case 3 for example of a resin formed into a capsule having a substantially oval longitudinal section. A front portion of case 3 is formed of a transparent member 3a. At the interior of the case 3, the encapsulated endoscope 2 has its main portion where the following members are disposed. In particular, disposed in a front portion facing the transparent member 3a are: a light source 6 for example of LED for illuminating an object to be taken such as a digestive organ within the body cavity; an observation optical system 8 (hereinafter referred to as objective lens) for forming an optical image of the object illuminated by the light source 6; and an area sensor 40 consisting for example of CCD or CMOS sensor for taking an image through the objective lens 8 and effecting predetermined photoelectric conversion processing to generate image signals. Disposed from there toward the back are: a light source drive control section 5 receiving output from the area sensor 40 for controlling light amount or light-emitting time of and driving the light source 6; a drive control/signal processing unit 9 having a drive control circuit and signal processing circuit of the area sensor 40; a communication unit 10 receiving image signals outputted from the drive control/signal processing unit 9 to transmit/output the same to a predetermined receiving/record ing apparatus (not shown) provided at the outside of the body cavity for example with using a wireless communication; and a power supply 4 consisting of power supply batteries 4a and 4b.

Of thus constructed encapsulated endoscope 2, the light source drive control section 5 determines light emitting conditions (emitting light amount and/or emitting time) of the light source 6 based on the output signals of the area sensor 40 and drives the light source 6 based on the determined light emitting conditions using the drive signals from the drive control/signal processing unit 9.

FIG. 4 shows drive timing (timing of light source drive current) of the light source 6 and the drive timing (timing of pixel region output) of the area sensor 40. In a dark part such as in the body cavity, light does not enter the area sensor 40 unless the light source 6 is caused to emit. In other words, the emitting time of the light source 6 is the exposure time of the area sensor 40. Accordingly, the exposure amount of the area sensor 40 can be controlled by controlling the light emitting conditions of the light source 6.

In the case where MOS imaging device is mounted on an encapsulated endoscope and the exposure amount is controlled at the light source, an electronic shutter function provided at an ordinary MOS imaging device is unnecessary because the interior of the body cavity is dark. On the other hand, there is a limit on the length and/or thickness of an encapsulated endoscope, since the encapsulated endoscope is to take images at the interior of the body cavity. For this reason, size reduction of MOS imaging device is a necessity when downsizing of the encapsulated endoscope is considered.

SUMMARY OF THE INVENTION

It is an object of the present invention to provide an encapsulated endoscope capable of further downsizing with mounting MOS imaging device having a suitable structure.

In a first aspect of the invention, there is provided an encapsulated endoscope including: MOS imaging device having a pixel section of a plurality of pixels disposed two-dimensionally in rows and columns, each pixel with a photo-diode and MOS transistor where a signal from the photodiode is amplified and outputted as a pixel signal, a sole and exclusive vertical scanning section for generating row select signals to select pixels of the pixel section by rows and to cause each pixel signal to be outputted to a plurality of vertical signal lines provided for each column, and a horizontal scanning circuit for causing selective outputting of each pixel signal outputted onto the plurality of vertical signal lines; an illumination light source section; a light source control section for controlling light emitting amount or emitting time of the illumination light source section; and a drive control/signal processing unit for controlling the light source control section to illuminate an object by said illumination light source section during a predetermined time and causing the pixel signals of said MOS imaging device to be outputted thereafter.

In a second aspect of the invention, the pixel section in the encapsulated endoscope according to the first aspect comprises a rectangular region with its center at a position corresponding to a substantial center of the MOS imaging device as a light-receiving pixel region, and a region surrounding the light-receiving pixel region as a light-blocked pixel region.

In a third aspect of the invention, the vertical scanning section in the encapsulated endoscope according to the first or second aspect has a first vertical scanning unit corresponding to odd rows of the pixel section and a second vertical scanning unit corresponding to even rows of the pixel section, the first vertical scanning unit and the second vertical scanning unit being disposed at regions opposing each other with the pixel section between them.

DESCRIPTION OF THE PREFERRED EMBODIMENTS

First Embodiment

Figure 3:
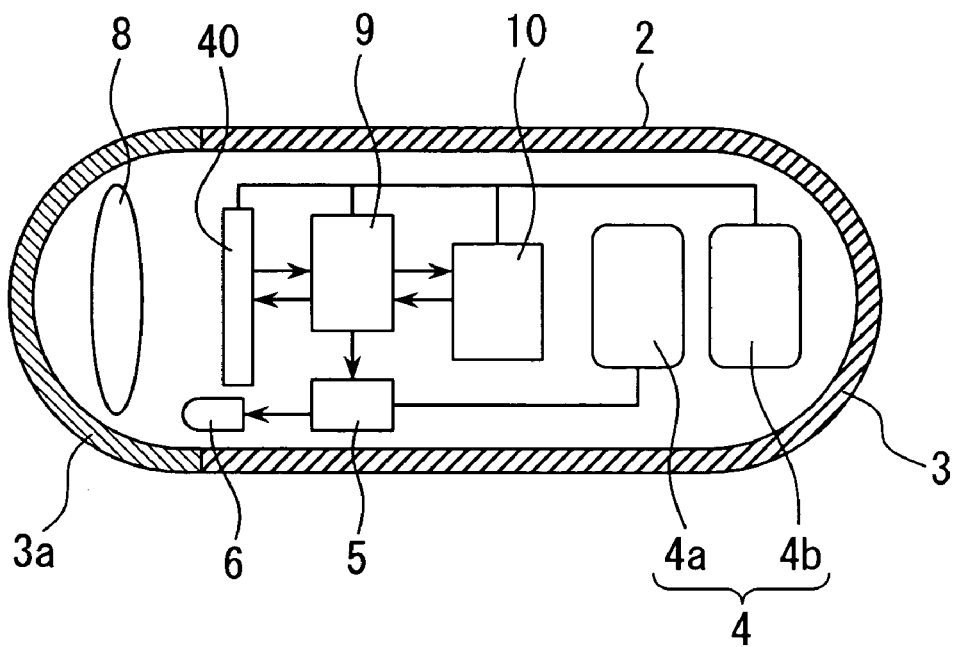
FIG. 3 is a block diagram schematically showing construction of the electrical circuit of a prior-art encapsulated endoscope.
Figure 4:
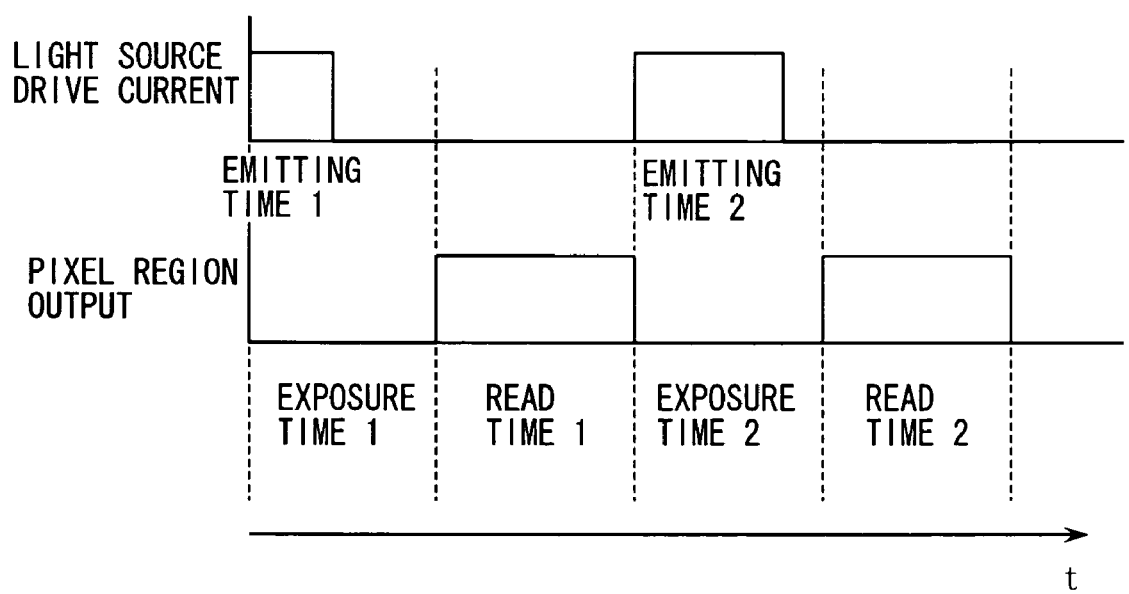
FIG. 4 is a timing chart for explaining light source drive period and read period of the prior-art encapsulated endoscope shown in FIG. 3.
Figure 5:
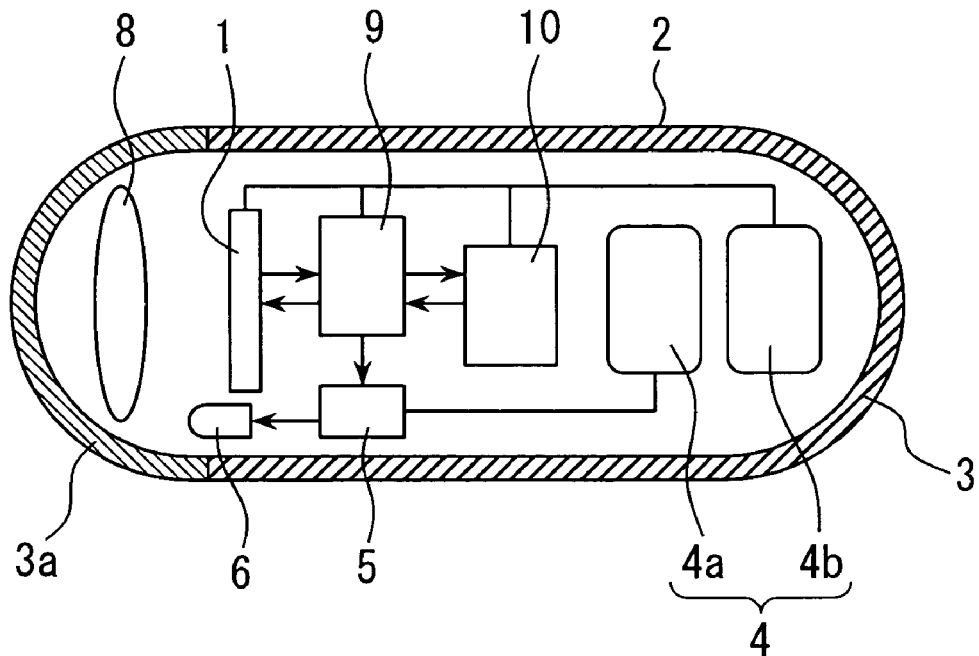
FIG. 5 is a block diagram schematically showing construction of the electrical circuit of an encapsulated endoscope according to a first embodiment of the invention.

A description will be given below of some embodiments with reference to the drawings. A first embodiment of the encapsulated endoscope according to the present invention will now be described. FIG. 5 is a block diagram schematically showing construction of the electrical circuit of an encapsulated endoscope 2 according to the first embodiment, where like or corresponding components as in the prior-art encapsulated endoscope 2 shown in FIG. 3 are denoted by like reference numerals. The construction and drive operation of the encapsulated endoscope according to the first embodiment shown in FIG. 5 are substantially identical to the construction and drive operation of the prior-art encapsulated endoscope shown in FIG. 3, and MOS image sensor 1 is suitably used as the area sensor therein. Further, since exposure amount thereof is controlled at the light source side, an exposure amount control at MOS image sensor 1 is not to be effected.

Figure 1:
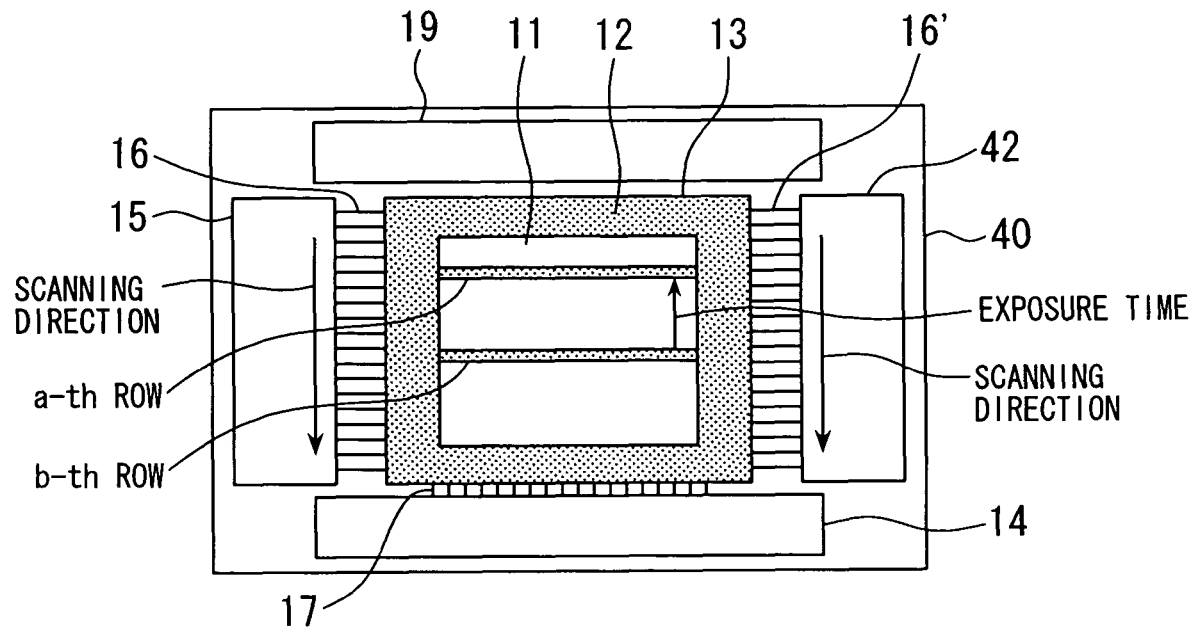
FIG. 1 is a block diagram schematically showing construction of a prior-art area sensor.
Figure 2:
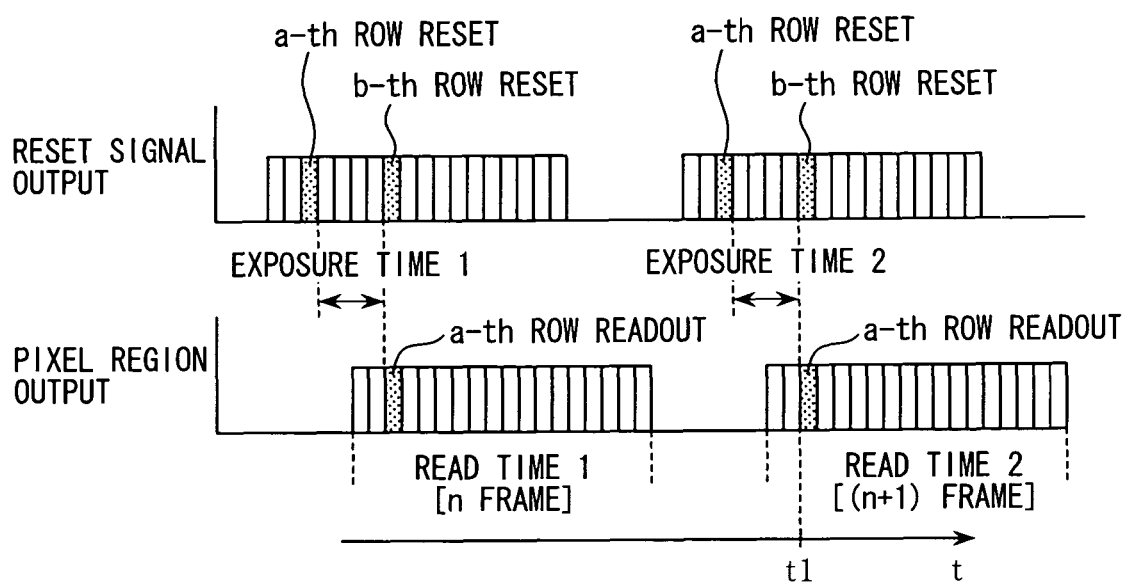
FIG. 2 is a timing chart for explaining reset period and read period in the prior-art area sensor shown in FIG. 1.
Figure 6:
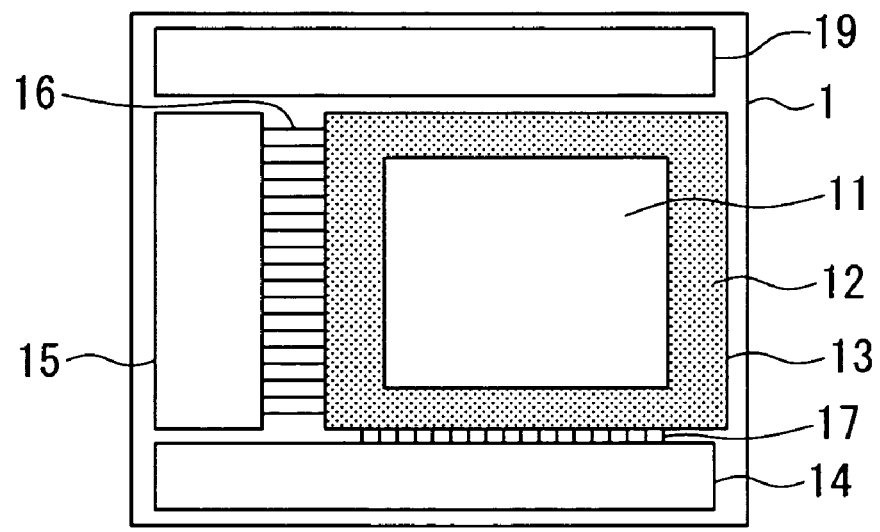
FIG. 6 is a top view schematically showing construction of MOS image sensor to be mounted on the encapsulated endoscope according to the first embodiment shown in FIG. 5.

FIG. 6 is a block diagram schematically showing construction of MOS image sensor 1 to be mounted on the encapsulated endoscope according to the first embodiment, where like or corresponding components as in the prior-art area sensor shown in FIG. 1 are denoted by like reference numerals. The MOS image sensor 1 includes: a pixel section 13 having a plurality of pixels two-dimensionally disposed in rows and columns, each pixel containing a photodiode for effecting photoelectric conversion and an amplifying MOS transistor where the optically produced charge generated at the photodiode is changed to voltage and amplified to be outputted; a read vertical scanning section 15 for selecting rows to be read out of the pixel signals of the pixel section 13 and sequentially switching the rows to be selected; a vertical scanning line 16 connecting between the pixel section 13 and the read vertical scanning section 15; a vertical signal line 17 to which the pixel signals of the read rows, selected at the read vertical scanning section 15 are outputted; a horizontal read circuit 14 for sequentially outputting the signals outputted onto the vertical signal line 17; and an operation control section 19 for controlling operation of MOS image sensor 1. The pixel section 13 consists of a light-receiving pixel region 11 and a light-blocked pixel region 12, and the vertical scanning section 15 is provided to the left of the pixel section 13.

Since exposure amount of the encapsulated endoscope 2 according to the first embodiment shown in FIG. 5 is controlled at the light source side, MOS image sensor 1 is not required to mount a vertical scanning circuit for electronic shutter which is to provide an exposure amount control function. Accordingly, due to the fact that a vertical scanning circuit for electronic shutter is not mounted, the sensor area can be made smaller as compared to the prior-art MOS image sensor so that size of the interior of the encapsulated endoscope can be reduced.

Second Embodiment

Figure 7:
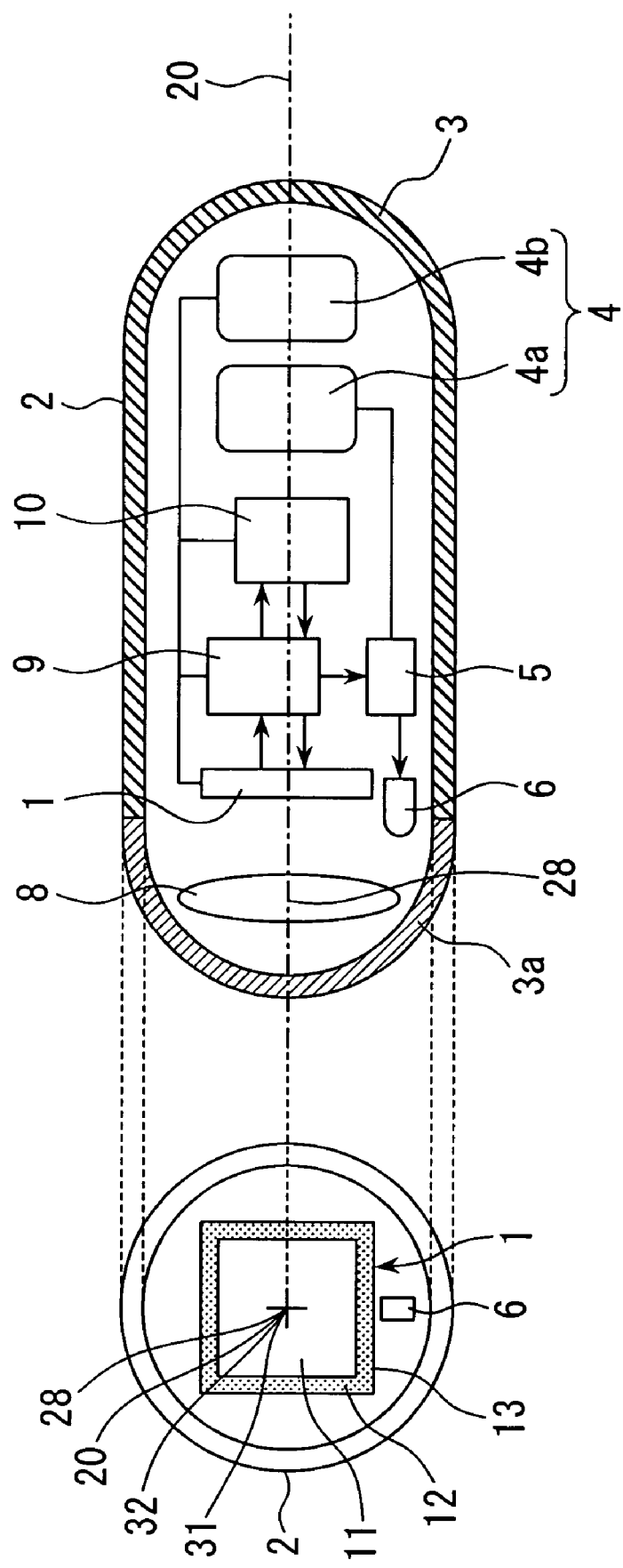
FIGS. 7A and 7B are a block diagram schematically showing construction of the electrical circuit of an encapsulated endoscope according to a second embodiment of the invention and a schematically shown front view as seen from the object side of the encapsulated endoscope, respectively.

A second embodiment of the invention will now be described. FIG. 7A is a block diagram schematically showing construction of the electrical circuit of an encapsulated endoscope 2 according to the second embodiment, where like or corresponding components as in the encapsulated endoscope according to the first embodiment shown in FIG. 5 are denoted by like reference numerals. The construction and drive operation of the encapsulated endoscope according to the second embodiment is identical to the construction and drive operation of the encapsulated endoscope according to the first embodiment shown in FIG. 5. FIG. 7B shows a front view as seen from the object side of the encapsulated endoscope 2 according to the second embodiment shown in FIG. 7A, where the center of MOS image sensor 1 is denoted by numeral 31, the center of the light-receiving pixel region 11 of the pixel section 13 by 32, the central axis of the encapsulated endoscope 2 by 20, and the center of the objective lens 8 by 28. It should be noted that FIG. 7B is a schematic representation of MOS image sensor 1.

As can be seen form FIG. 7B, a substantial coincidence in disposition is achieved of the central axis 20 of the encapsulated endoscope 2, center 31 of MOS image sensor, center 32 of the light-receiving pixel region of the pixel section 13, and center 28 of the objective lens 8.

Figure 8:
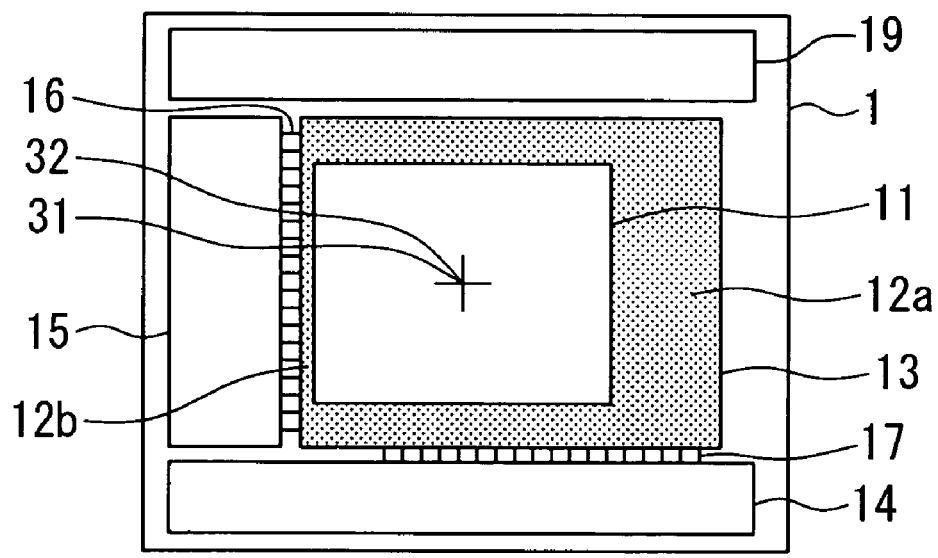
FIG. 8 is a block diagram showing construction of MOS image sensor to be mounted on the encapsulated endoscope according to the second embodiment.

FIG. 8 is a block diagram showing construction of MOS image sensor 1 to be mounted on the encapsulated endoscope according to the second embodiment. Although the fundamental construction of MOS image sensor according to the second embodiment is identical to the MOS image sensor 1 according to the first embodiment shown in FIG. 6, there is a difference in that a light-blocked pixel region 12a on the side opposite to the side on which the vertical scanning section 15 of the pixel section 13 is located is made wider as compared to a light-blocked pixel region 12b on the vertical scanning section 15 side, thereby a substantial coincidence is achieved of the center 31 of MOS image sensor 1 and the center 32 of the light-receiving pixel region 11.

The shape of the objective lens 8 in the encapsulated endoscope is a factor in determining the shape of the encapsulated endoscope 2. To reduce the size of the encapsulated endoscope 2, it is desirable that the objective lens 8 be disposed within the capsule case 3 as shown in FIG. 7B so that the center 28 of the objective lens 8 and the central axis 20 of the encapsulated endoscope 2 substantially coincide. For this reason, MOS image sensor 1 as shown in FIG. 8 is disposed in the encapsulated endoscope 2 so that the center 31 thereof and the central axis 20 of the encapsulated endoscope 2 substantially coincide, so as to result the construction of the encapsulated endoscope where a substantial coincidence is achieved of the center 31 of MOS image sensor 1, the center 32 of light-receiving pixel region 11, the central axis 20 of the encapsulated endoscope 2, and the center 28 of the objective lens 8. It is thereby possible to effectively use the space at the interior of the encapsulated endoscope, and a further downsizing of the encapsulated endoscope is feasible.

Also from the viewpoint of packaging, since the center 31 of MOS image sensor 1 and the center 32 of light-receiving pixel region 11 substantially coincide, an extra space is not required in the positioning of MOS image sensor 1 with respect to the observation optical system. A further downsizing of the encapsulated endoscope is thereby possible.

Third Embodiment

Figure 9:
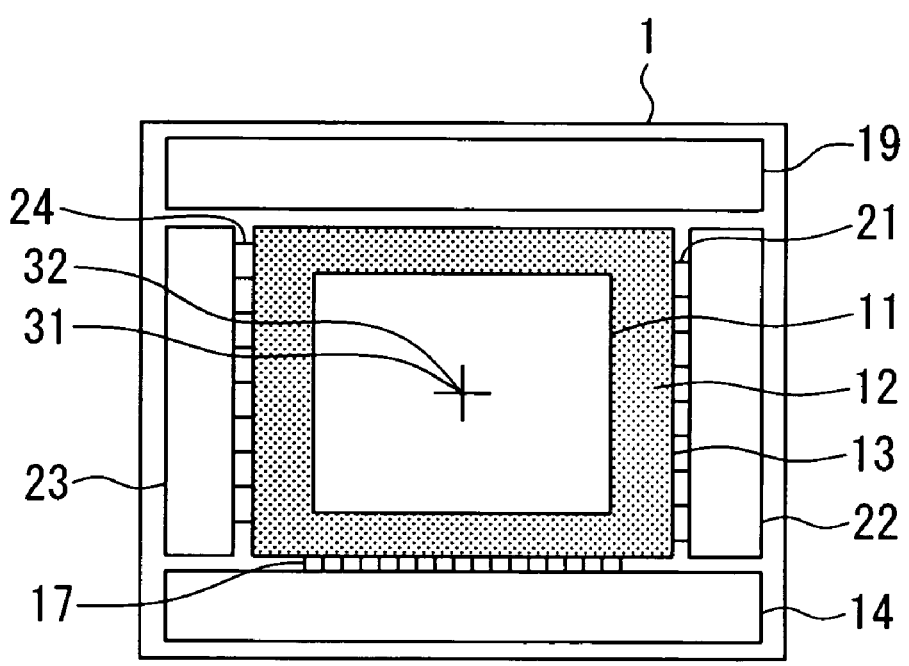
FIG. 9 is a block diagram showing construction of MOS image sensor to be mounted on an encapsulated endoscope according to a third embodiment of the invention.

A third embodiment of the invention will now be described. FIG. 9 is a block diagram showing construction of MOS image sensor 1 to be mounted on an encapsulated endoscope 2 according to the third embodiment. The MOS image sensor 1 according to the third embodiment includes: a pixel section 13 having a plurality of pixels two-dimensionally disposed in rows and columns: a first vertical scanning unit 23 for selecting odd rows to be read of the pixel signals of the pixel section 13 and for sequentially switching the row to be selected; a first vertical scanning line 24 for connecting between the pixel section 13 and the first vertical scanning unit 23; a second vertical scanning unit 22 for selecting even rows to be read of the pixel signals of the pixel section 13 and for sequentially switching the row to be selected; a second vertical scanning line 21 for connecting between the pixel section 13 and the second vertical scanning unit 22; a vertical signal line 17 onto which the pixel signals of the row to be read, selected at the first vertical scanning unit 23 and the second vertical scanning unit 22 are outputted; a horizontal read circuit 14 for sequentially outputting the signals outputted onto the vertical signal line 17; and an operation control unit 19 for controlling operation of MOS image sensor 1.

The pixel section 13 consists of a light-receiving pixel region 11 and a light-blocked pixel region 12. The first vertical scanning unit 23 is provided to the left side of the pixel section 13 while the second vertical scanning unit 22 is provided to the right side of the pixel section 13. Since exposure amount is controlled at the light source side, a vertical scanning circuit for electronic shutter is not mounted. Further, it is constructed so as to achieve coincidence of the center 31 of MOS image sensor 1 and the center 32 of light-receiving pixel region 11. It should be noted that the first and second vertical scanning units 22, 23 constitute a vertical scanning section.

Figure 10:
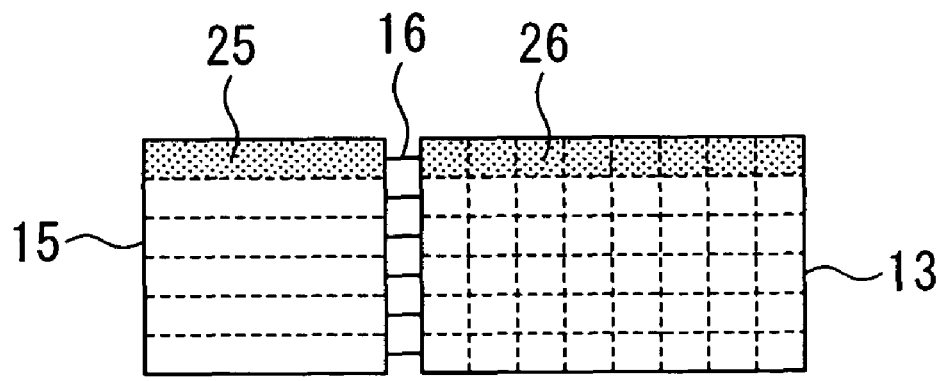
FIG. 10 is a block diagram schematically showing the construction of pixel section and vertical scanning section of MOS image sensor in the encapsulated endoscope according to the first embodiment shown in FIG. 6.

In order to explain construction of the first and second vertical scanning units of MOS image sensor and mode of connection between the pixel section and the first and second vertical scanning units of the third embodiment, a description will be first given by way of FIG. 10 of construction of the vertical scanning section 15 of MOS image sensor 1 and connecting mode of the vertical scanning line 16 for connecting between the pixel section 13 and the vertical scanning section 15 in the first embodiment shown in FIG. 6. In the connecting mode of the first embodiment shown in FIG. 10, a scanning stage part of the vertical scanning section corresponding to one row of the vertical scanning section 15 conforms to one row of the pixel section 13, where a light-receiving region corresponding to one row of the pixel section 13 is denoted by numeral 26, and a scanning stage part of the vertical scanning section corresponding to one row is denoted by numeral 25.

Figure 11:
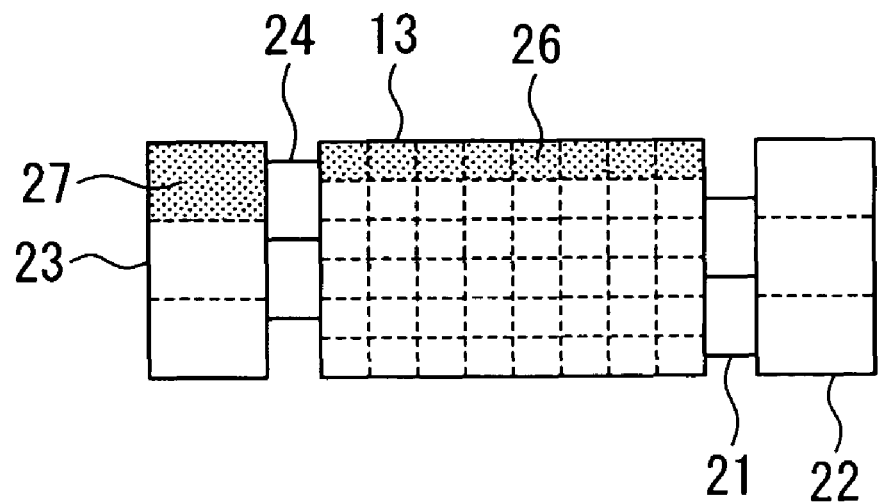
FIG. 11 is a block diagram schematically showing construction of the pixel section, first vertical scanning unit, and second vertical scanning unit of MOS image sensor in the encapsulated endoscope according to the third embodiment shown in FIG. 9.

Of MOS image sensor 1 in the third embodiment shown in FIG. 9, FIG. 11 shows construction of the pixel section 13 and the first vertical scanning unit 23, the connecting mode of the first vertical scanning line 24 for connecting between the pixel section 13 and the first vertical scanning unit 23, construction of the second vertical scanning unit 22, and the connecting mode of the second vertical scanning line 21 for connecting between the pixel section 13 and the second vertical scanning unit 22. In the third embodiment shown in FIG. 11, a scanning stage part of one row of the first vertical scanning unit 23 corresponds to one row of the odd rows of the pixel section 13, and a scanning stage part of one row of the second vertical scanning unit 22 corresponds to one row of the even rows of the pixel section 13. A light-receiving region corresponding to one row of the odd rows of the pixel section 13 is denoted by numeral 26, and a scanning stage part of the first vertical scanning unit 23 corresponding to one row of the odd rows by 27.

Of the MOS image sensor according to the third embodiment as shown in FIGS. 9 and 11, the first vertical scanning unit 23 for selecting odd rows and the second vertical scanning unit 22 for selecting even rows are disposed to the left side and to the right side, respectively, of the pixel section 13. An extent of width corresponding to two rows of the pixel section 13 can be secured as the vertical length of each scanning stage part of the first and second vertical scanning units 22, 23 that is necessary for scanning of one row of the pixel section 13.

For this reason, as shown in FIG. 11, the horizontal length of the first vertical scanning unit 23 and the second vertical scanning unit 22 in MOS image sensor according to the third embodiment can be made shorter as compared to the vertical scanning section 15 in MOS image sensor according to the first embodiment shown in FIG. 10.

By suitably disposing the circuits, then, the horizontal length of the vertical scanning section 15 of MOS image sensor according to the first embodiment and the horizontal length combining the first vertical scanning unit 23 and the second vertical scanning unit 22 of MOS image sensor according to the third embodiment can be made substantially the same so that an area increase of MOS image sensor 1 may be reduced to a minimum.

By disposing MOS image sensor 1 according to the third embodiment having such construction into the encapsulated endoscope 2 according to the second embodiment 2 shown in FIG. 7A so that the center 31 of MOS image sensor 1 and the central axis 20 of the encapsulated endoscope 2 substantially coincide, the encapsulated endoscope 2 is obtained as having construction where a substantial coincidence is achieved of the center 31 of MOS image sensor 1, the center 32 of the light-receiving pixel region 11, the central axis 20 of the encapsulated endoscope 2, and the center 28 of the objective lens 8. An effective use of the space at the interior of the encapsulated endoscope is thereby possible, and a further downsizing of the encapsulated endoscope 2 is feasible.

In the encapsulated endoscope according to the third embodiment, since the center 31 of MOS image sensor 1 and the center 32 of the light-receiving pixel region 11 coincide, the positioning of MOS image sensor 1 with respect to an observation optical system at the time of packaging can be effected without requiring an extra space. For this reason, a further downsizing of the encapsulated endoscope 2 is possible. Further, the degree of freedom is increased of the disposition of the light-receiving pixel region 11 and the light-blocked pixel region 12 in the case where coincidence is achieved of the center 31 of MOS image sensor 1 and the center 32 of the light-receiving pixel region 11.

As has been described by way of the above embodiments, in accordance with the first aspect of the invention, the exposure amount control of MOS imaging device is effected by a light-source control section, and by a sole vertical scanning section, row select signals having one-to-one correspondence to each row of the pixel section are generated without providing a vertical scanning section for electronic shutter which has conventionally been disposed as a separate vertical scanning circuit for example at a position opposite to a vertical scanning section with the pixel section between them. A downsizing of the encapsulated endoscope is possible by using MOS imaging device having the sole vertical scanning section where thus generated row select signals are the signals for designating the rows to be read out of the pixel signals.

In accordance with the second aspect of the invention, since the center of the light-receiving pixel region of the pixel section and the center of MOS imaging device substantially coincide, the positioning of MOS imaging device with respect to the encapsulated endoscope can be effected without requiring an extra space, whereby a further downsizing of the encapsulated endoscope is possible. In accordance with the third aspect of the invention, since it is readily possible to achieve coincidence of the center of the light-receiving pixel region and the center of MOS imaging device, the positioning of MOS imaging device with respect to the encapsulated endoscope is easy without requiring an extra space, whereby a further downsizing of the encapsulated endoscope is possible.

What is claimed is:

1. An encapsulated endoscope comprising:
MOS imaging device having a pixel section of a plurality of pixels disposed two-dimensionally in rows and columns, each pixel with a photodiode and MOS transistor where a signal from the photodiode is amplified and outputted as a pixel signal, a sole and exclusive vertical scanning section for generating row select signals to select pixels of said pixel section by rows and to cause each pixel signal to be outputted to a plurality of vertical signal lines provided for each column, and a horizontal scanning circuit for causing selective outputting of each pixel signal outputted onto said plurality of vertical signal lines;
an illumination light source section;
a light source control section for controlling light emitting amount or emitting time of said illumination light source; and
a drive control/signal processing unit for controlling said light source control section to illuminate an object by said illumination light source section during a predetermined time and causing the pixel signals of said MOS imaging device to be outputted thereafter;
wherein said pixel section comprises a rectangular region with its center at a position corresponding to a substantial center of said MOS imaging device as a light-receiving pixel region, and a region surrounding said light-receiving pixel region as a light-blocked pixel region;
wherein said light-blocked pixel region comprises a first region located on the side on which said sole and exclusive vertical scanning section is located and a second region located on the side opposite to the side on which said sole and exclusive vertical scanning section is located, and
said second region is configured wider as compared to said first region so that the center of said MOS imaging device, the center of light-receiving pixel region and a central axis of the encapsulated endoscope are substantially coincident, and
said encapsulated endoscope further comprising an observation optical system, wherein a center of the observation optical system and a center of said MOS imaging device occur on a center axis of a capsule.

* * * * *